Dec. 15, 1942. Q. A. S. McKEAN Plant Pat. 559
HELIOTROPE PLANT
Filed Nov. 15, 1941
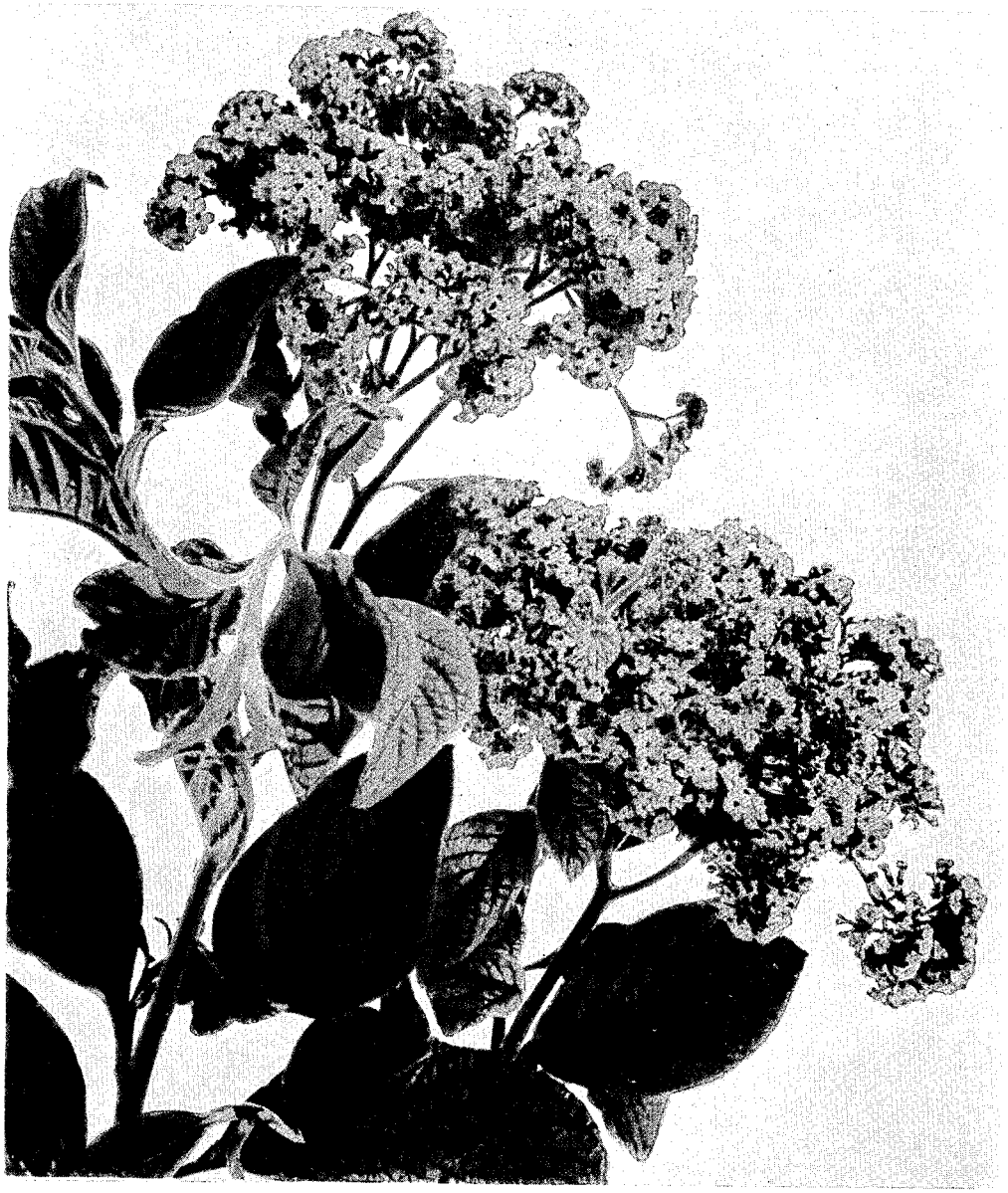
Inventor
Q. A. S. McKean
By Robb & Robb
Attorneys Patented Dec. 15, 1942

Plant Pat. 559

UNITED STATES PATENT OFFICE

559

HELIOTROPE PLANT

Quincy A. Shaw McKean, Prides Crossing, Mass.

Application November 15, 1941, Serial No. 419,351

1 Claim. (Cl. 47—60)

The present discovery relates to a new and distinct variety of heliotrope plant.

Historically speaking, and having reference to the origin of this variety, while in Guatemala a number of years ago, I came upon a heliotrope plant that attracted my attention because it was so completely different from anything in the line of heliotropes I had ever seen theretofore. I was assured that the seed of this plant would not germinate, but nevertheless, I brought back to the United States with me hundreds of seeds from this plant. I was successful, however, only in raising three seedlings from all of these hundreds of seeds, and these failed to come true to the original plant and each differed from the other. The great attractiveness of these three seedlings warranted preservation for they proved to be of a deeper, richer color shade of flower and foliage than the original or parent plant from which the seeds were taken, as above mentioned.

Therefore, I asexually reproduced a goodly number of plants from each of the three seedlings, and grew these groups separately over a period of years to determine which of the three groups had the best growing habits. During this period of determination, I made consistent effort to determine also whether seeds from any of the three seedling plants mentioned could be made to germinate, but was wholly unsuccessful.

From these three distinct groups above referred to, I selected the one group which I thought was most satisfactory, and that constitutes the variety herein disclosed. All other plants were destroyed. The plants of the new variety invariably come true to form by asexual reproduction.

It will therefore be understood that the following description sets forth the established characters of this new variety, propagated entirely from cuttings, which shows a vigorous luxuriant growth, tender or half-hardy when grown outdoors in northern latitudes. As above indicated the seeds of this variety have not been found to be viable.

The most distinguishing feature of this new heliotrope variety is its unique deep flower color, darker than any other variety known at this date. The foliage also, in its deep and heavy veinings, extra large leaves and very dark, metallic, and blackish violet-green suffusion is unique.

More generally speaking, the plant is adapted to pot culture, but may be grown to standard or tree form, or it may be grown as a border, bedding or specimen plant.

Flowering is continual and continuous, from sizable plants in spring until frosts in autumn, and may then be taken indoors for winter blooming.

It roots readily and quickly from soft-wood cuttings, growing best in rather rich, mellow, loose, moist soil.

Taking up now the more specific aspects of this new variety, the distinguishing features thereof include a more vigorous, luxuriant growth as hereinbefore mentioned; larger, oblong-lanceolate, simple, pinnately veined, deeply crimped, wrinkled, rough veined or corrugated leaves; darker and richer colored flowers than other varieties or hybrids of the species or other species of heliotrope; and more odoriferous or with stronger fragrance to the flowers than with other large-leaved heliotrope varieties.

Plants reach 3 or more feet in height in one season outdoors, branching freely from each leaf axil, and forming stocky, bushy, self-supporting growth. Leaves, even on young plants, will measure to 5 inches or more in length, by 2¼ or more inches in width. Leaves are borne alternately but in almost opposite positions, alternate pairs being practically at right angles, but leaves appearing spirally arranged on the stem when viewed from above.

The stocky stems and the petioles attain a rich and dark bronzy violet coloring which is also carried in a metallic sheen or lustre to the upper surface of the leaves, and stems are lightly covered with short, white, bristly hairs, giving a somewhat gelatinous feel to the touch.

Flowers are borne in very large terminal corymbs of coiled racemes and cymes, individual florets measuring about $\frac{3}{16}$ inch in diameter and borne in indeterminate clusters, corymbs reaching to 6 inches and more across. Flowers are uniformly of darker color under outdoor growing conditions, a blackish violet, and which is considered the true color. The color lightens to dark violet and fluorite-violet and to mulberry-purple on ageing; lighter under hot-house conditions.

According to Ridgway's Color Standards and Nomenclature, nearest matching of colors are as follows:

Stems and unopened buds:
- Olivaceous Black, Plate XLVII.

Opening buds:
- Prune Purple, Plate XI.

Flowers:
- Mulberry Purple, Plate XI.
- Fluorite Violet, Plate XI.
- Dark Violet, Plate X.
- Blackish Violet, Plate X.

Leaves, young:

*Upper surface.*—Forest Green, Plate XVII.

*Under surface.*—Kronberg's Green, Plate XXXI.

Leaves, mature:

*Upper surface.*—Ivy Green, Plate XXXI, Dusky Olive-Green, Plate XLI.

*Under surface.*—Pois Green, Plate XLI.

It is to be understood that although the description given herein above accurately represents and describes the new variety of plant, the general characteristics may vary slightly due to climatic conditions, soil, etc.

I claim:

A new and distinct variety of heliotrope plant, characterized as to novelty by its vigorous, luxuriant growth, its unique deep flower color, and the extra large foliage with deep and heavy veinings and very dark coloring, substantially as described and shown.

QUINCY A. SHAW McKEAN.